United States Patent [19]
Hines

[11] Patent Number: 5,503,553
[45] Date of Patent: Apr. 2, 1996

[54] ORAL HYGIENE DEVICE

[76] Inventor: John E. Hines, 10 Skysail Ct., Sacramento, Calif. 95831

[21] Appl. No.: 426,209

[22] Filed: Apr. 21, 1995

[51] Int. Cl.$^6$ ................................................. A61G 17/02
[52] U.S. Cl. ............................................. 433/80; 601/162
[58] Field of Search ................................. 433/80, 82, 85, 433/216; 601/141, 162

[56] References Cited

U.S. PATENT DOCUMENTS

| | | | |
|---|---|---|---|
| 3,400,999 | 9/1968 | Goldstein | 433/82 |
| 4,276,023 | 6/1981 | Phillips et al. | 433/82 X |
| 4,672,953 | 6/1987 | DiVito | 433/80 X |
| 4,770,632 | 9/1988 | Ryder et al. | 433/80 X |
| 5,062,413 | 11/1991 | Bullard | 601/162 |

*Primary Examiner*—Nicholas D. Lucchesi
*Attorney, Agent, or Firm*—Lothrop & West

[57] ABSTRACT

In order to take care of the oral hygiene needs of aged or infirm patients in health care facilities, or the like, a relatively small, compact, self-contained device can be carried by a lay operator from room to room. Fresh water in one container carried on the device is replenished from each room's fresh water faucet and waste water in another container is disposed of in the room's sink. Each patient has an individual tooth brush adapted to engage a handle connected by flexible tubing to the portable device and suitable switches enable the operator to control the operation of electrically actuated components effective to discharge fresh water through the bristles of the brush and vacuum waste water from the vicinity of the brush tip end. Particular care is built into the design of the unit to prevent cross-contamination and electrical shock hazard.

7 Claims, 6 Drawing Sheets

ORAL HYGIENE DEVICE

BACKGROUND INFORMATION

1. Field of the Invention

The invention relates to portable, self-contained units which can be carried to individual patients, or occupants, of health care facilities, or the like, in order to attend to the individual's oral hygiene requirements.

2. Prior Art

Applicant is unaware of any patents, or other publications, or of any existing devices designed to provide individualized oral hygiene in a health care facility environment.

SUMMARY OF THE INVENTION

A preferred embodiment of the invention comprises a relatively small, light-weight, compact, unit which can be carried by a lay operator from patient to patient in a convalescent home, for example, where, in many cases, the patients are unable to keep their teeth and mouths clean either as a result of old age or medical infirmity.

The unit includes a console, or housing, enclosing a fresh water supply container constructed to permit convenient replenishment with fresh water from the basins installed in most patients' rooms and a waste water container adapted to receive used water removed by vacuum from the patient's mouth.

Each patient is provided with his or her own toothbrush and the construction of the device as well as the procedure to be followed are both designed to prevent cross-contamination. If cost is not a consideration, the toothbrush can be discarded after each use and a new one used the next time.

Although susceptible of being operated by battery power, weight is saved while maintaining freedom from electrical shock hazard as a result of reducing the voltage at the room's wall outlet to low voltage, on the order of 12 volts for energizing various components.

The device pumps fresh water from the fresh water container through the bristles of the patient's toothbrush while brushing the teeth. At the same time, waste water in the mouth is vacuumed out of the mouth and deposited in the waste water container in the console, thus enabling the patient to avoid having to expel waste water and debris from the mouth in an intermittent and often inconvenient fashion.

Waste water in the waste water container is emptied into the basins or sinks, in the patients' rooms, as and when required. A warning light alerts the operator when it is time to empty the waste water container.

BRIEF DESCRIPTION OF THE DRAWING FIGURES

DETAILED DESCRIPTION OF THE INVENTION

Figure 1:
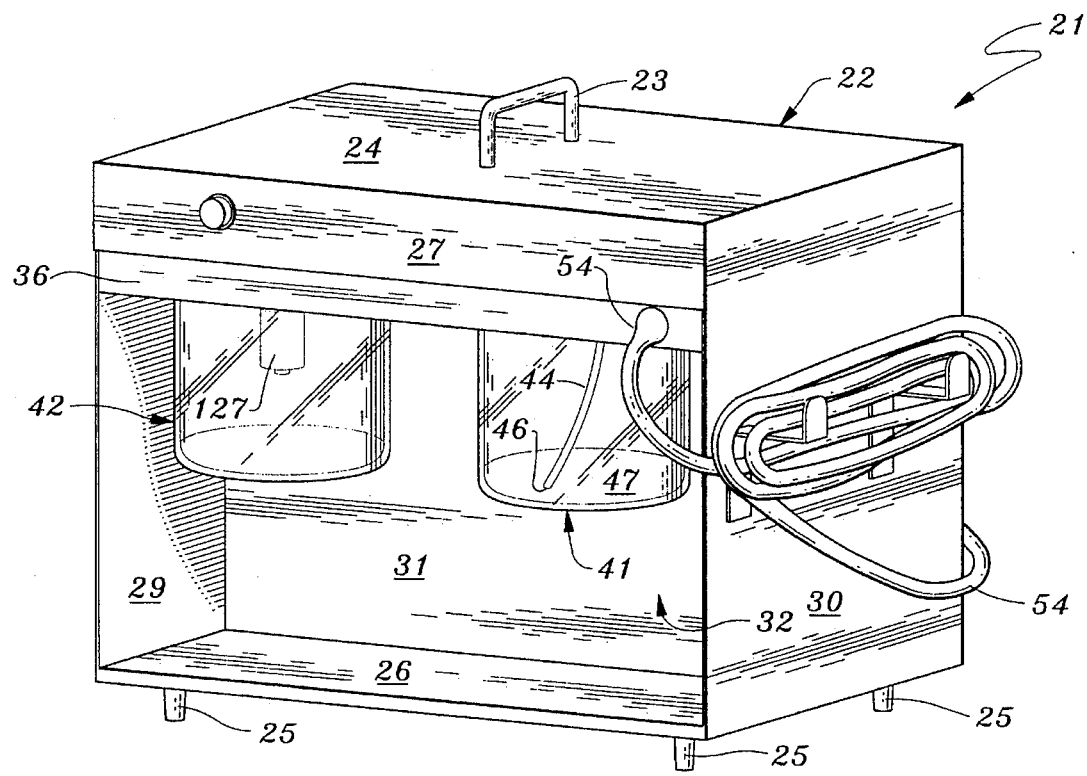
FIG. 1 is a top right front perspective view, to a reduced scale, of the console showing, from left to right, the waste water container, the fresh water container and the conduit leading from the container manifold toward the rear of the console.

For convenience in carrying the oral hygiene device of the invention 21 from patient to patient a console 22, or housing, is provided with a handle 23 on the top cover 24. At rest, the console 22 is supported on cushioned feet 25 on a bottom panel 26.

The console 22 extends in depth between the vertical planes of a partial front panel 27 and a vertical full rear panel 28, and in width, between a vertical left panel 29 and a vertical right panel 30.

A vertical mounting plate 31 is mounted parallel to the front panel 27 and the rear panel 28 and separates the water container compartment 32 from the pump and electrical components compartment 33 of the console 22.

The top surface of the mounting plate 31 provides support for the rear end of a thick horizontal plate 34, or block, of a dense plastic material, such as Delrin. The block 34 is formed with various internal passageways and fittings and serves as a bottle or container manifold 36, as will subsequently be described in detail.

Figure 3:
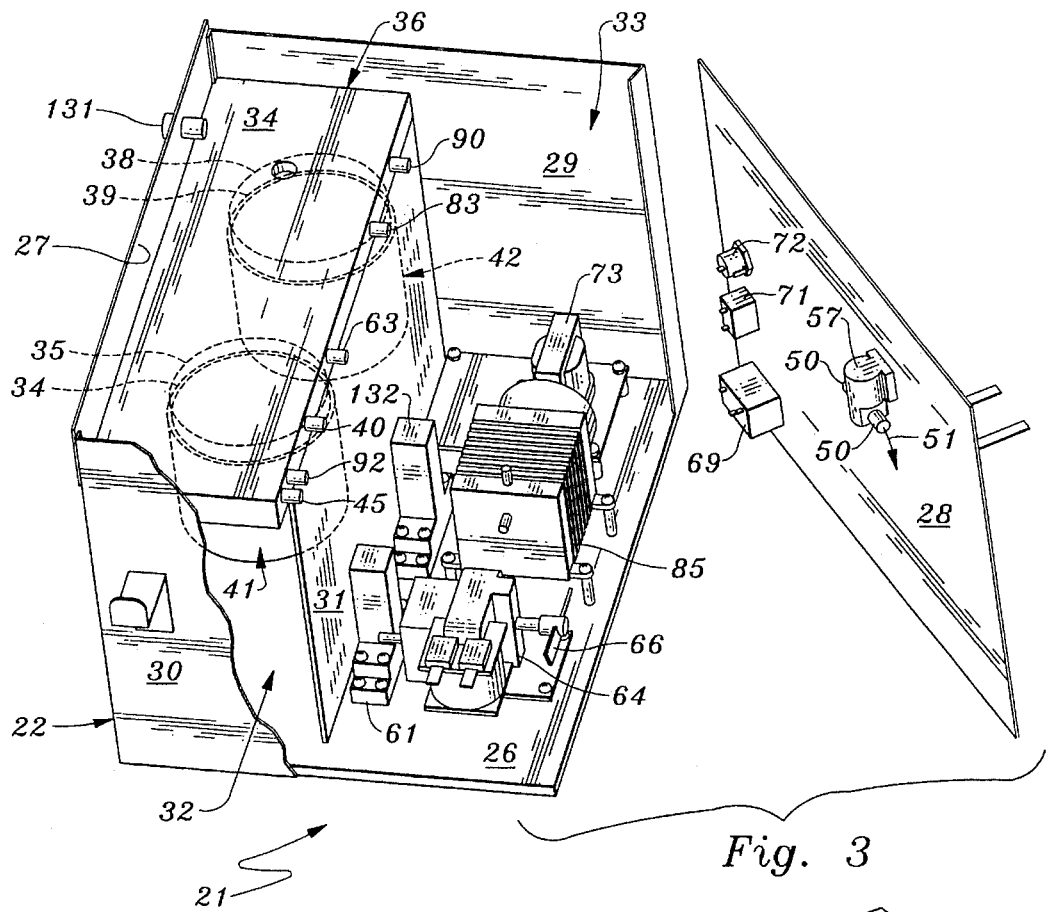
FIG. 3 is a top right rear perspective view of the console with the rear panel removed and slightly repositioned and with the top cover and portions of the console broken away to reveal interior details.

The console 22 and attendant components housed thereby are carried by the operator from room to room in a convalescent home, for example. In most such facilities each room is provided with a basin with a fresh water tap which can be used by the operator to fill a transparent fresh water supply container 41, or dispenser bottle. The container 41 is detachably mounted, by any suitable arrangement on the bottom of the manifold 36, as best appears in FIGS. 3 and 4. A preferred connection comprises a threaded fitting including a threaded top 35 on the container 41 and a threaded socket 37 on the bottom of the manifold 36.

In similar fashion, a transparent waste water container 42, or receptacle, or receiver bottle, is detachably secured to the bottom surface of the manifold 36 by a threaded fitting including a threaded top 38 on the receptacle 42 and a threaded socket 39 on the manifold 36.

In order to provide a fresh water supply, fresh water 43 is conducted from the fresh water container 41 in the following manner. A feed tube 44 extends from an open tip 46, located slightly above the bottom 47 of the container 41, upwardly to a fitting 48 on the horizontal surface of the manifold socket 37 (see FIGS. 4 and 5). From the fitting 48, fresh water 43 under pressure flows through a fore and aft bore 49 in the manifold 36 and emerges through a fitting 40 into tubing 50, thence through the tubing 50, in the direction of the arrow 51, to enter a fitting 45 connected to a bore 52 in the manifold 36. From the bore 52, the fresh water emerges from the manifold 36 and enters fresh water supply tubing 53.

As most clearly appears in FIGS. 1, 2, 5–7 and 12, the tubing 53 is sheathed by a flexible conduit 54, or duct, or tubing, extending to a brush handle 56, as will subsequently be described in more detail. The flexible duct 54 also sheathes a waste water tubing 55 and a pair of insulated electrical conductors 59.

Figure 4:
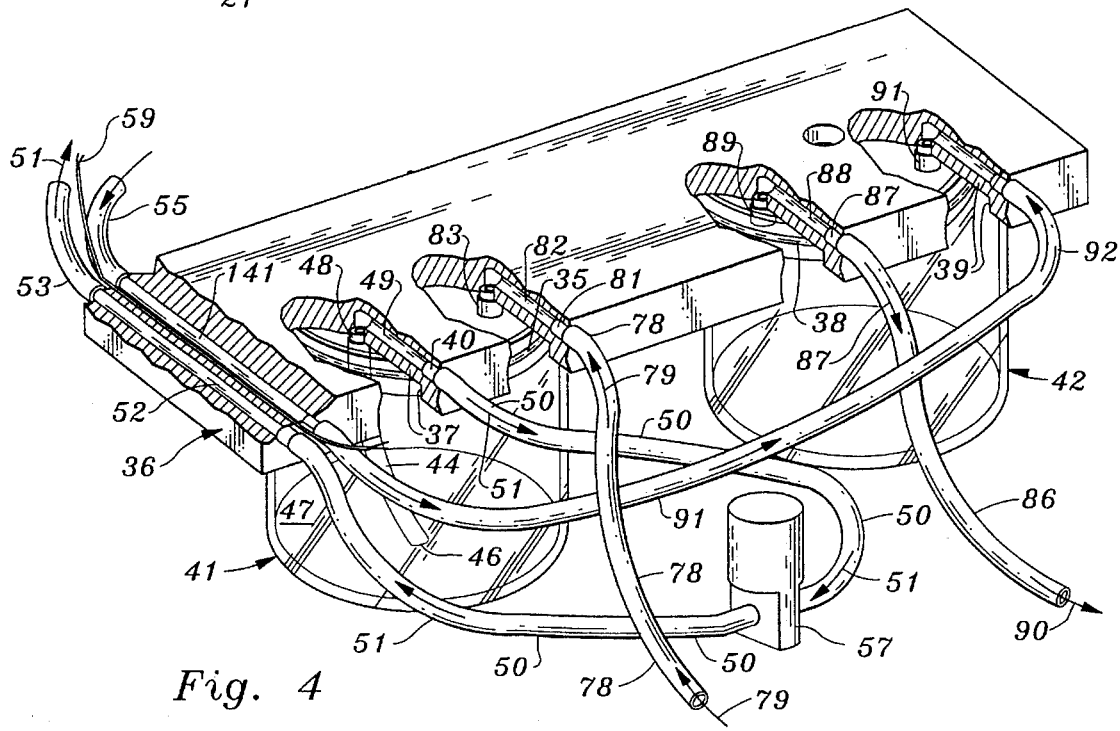
FIG. 4 is a top right rear perspective view, to an enlarged scale, of the feed and waste water manifold, with portions broken away to disclose interior structural details.

The flow 51 of fresh water 43 is controlled by a normally closed shut-off valve 57 interposed in the tubing 50, as best appears in FIG. 4. The ON-OFF positions of the shut-off valve 57 are electrically regulated by a water supply switch 58 (see FIGS. 8, 10 and 14) located on the forward end portion of the brush handle 56 for ease of manipulation by the operator. The manually operated ON-OFF switch 58 is connected by the pair of insulated electrical conductors 59 extending through the conduit 54 and the manifold 36 to a first relay 61 (see FIGS. 3 and 14) governing the position of the shut-off valve 57 interposed in the fresh water supply tubing 50 (see FIG. 4).

Fresh water 43 in the fresh water supply container 41 (see FIG. 5) is preferably replenished prior to the commencement of each oral hygiene cycle. Replenishment is usually effected by unscrewing the fresh water container 41 from the threaded socket 37 in the bottom of the manifold block 34 and holding the container 41 under the faucet of the basin, or sink, in the patient's room until the fresh water surface 63 is at the approximate level shown in FIG. 5. The container 41 is then screwed back into the respective socket 37 far enough to effect a tight seal with a rubber gasket, not shown, located in the socket 37.

At this juncture, the open bottom 46 of the fresh water feed tube 44 is slightly above the bottom 47 of the container 41 and the fresh water 43 is ready to be supplied as soon as (a) the container 41 is air-pressurized and (2) the normally closed water supply shut-off valve 57 is opened by actuation of the water supply switch 58 on the brush handle 56 which energizes a relay 61 connected to the switch 58.

Pressurization of the fresh water supply container 41 is attained by operation of an air pressure pump 64 (see FIGS. 3 and 14) mounted on the bottom panel 26 of the console 22. The pressure pump 64 is cooled by a propeller-type fan 66 and is electrically connected to a 115v. power supply by a power cord 68 and associated fitting 69 (see FIG. 2).

A main power switch 71 with fuse 72 controls the ON-OFF condition of the entire unit whereas the water supply switch 58 on the brush handle 56 governs the ON-OFF status of the pressure pump 64 as well as the water supply shut-off valve 57.

A transformer 73 mounted on the bottom panel 26 receives power at 115v. from the main power supply and, through a rectifier 74 and regulator 75 (see FIG. 14), reduces the voltage of the output to 12 volts D.C. for reasons of safety.

In other words, current at a very low voltage is led by conductor 59 from the voltage regulator 75 to the water supply ON-OFF switch 58 on the brush handle 56 and thence to the combined air pressure pump and shut-off valve relay 61.

When the water supply switch 58 on the handle 56 is in OFF position, the normally closed water supply shut-off valve 57 is in CLOSED condition and the air pressure pump 64 is in OFF condition.

When, on the other hand, the water supply switch 58 is pressed, against spring bias, into ON position, the 12 volt power supply operates the control relay 61 both to open the shut off valve 57 and to turn on the air pressure pump 64, causing the pump 64 to operate at its designed 115 voltage. The air pump 64 causes air to flow through the tubing 78 (see FIG. 4) in the direction of the arrow 79, through the manifold fitting 81, the bore 82 and the emitter 83, thence into the fresh water supply container 41 where the pressurized air superimposed on the top of fresh water 43 urges the water into the tube 44 for flow, as previously explained, to the brush handle 56.

Figure 14:
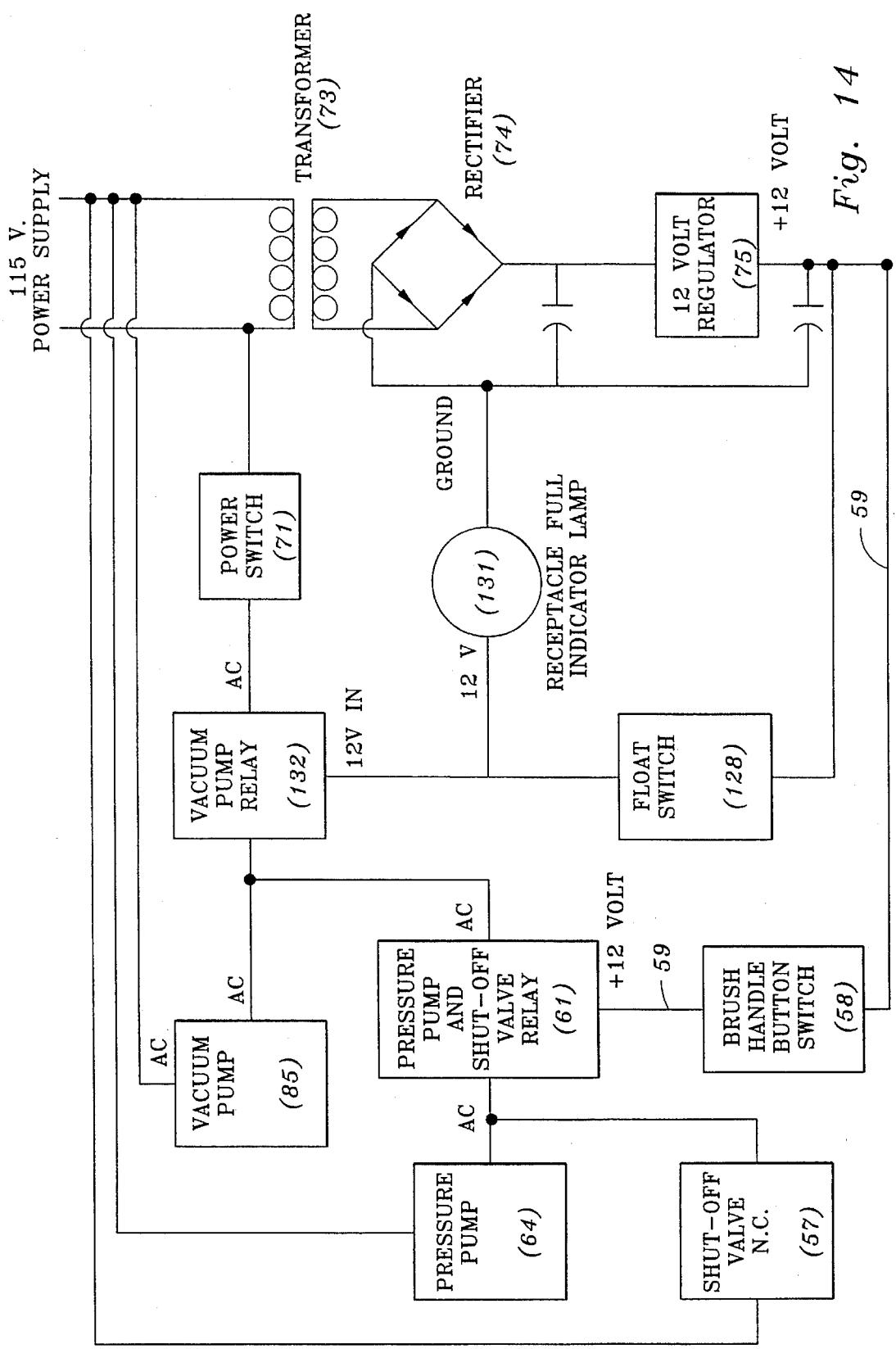

The waste water system operates on a vacuum induced in the waste water receptacle 42 by a vacuum pump 85 connected to the 115 v. power supply as shown in FIG. 14. The vacuum pump 85 commences to operate as soon as the main power switch 71 is placed in ON position.

The vacuum pump 85 is connected, through tubing 86, fitting 87, bore 88 and fitting 89 to the interior of the waste water receptacle 42 (see FIG. 4). Thus, by withdrawing air from the receptacle 42 through the tubing 86 in the direction of the arrow 90, a sub-atmospheric pressure, or "vacuum" is established inside the receptacle 42.

This "vacuum" within the waste water receptacle 42 exerts a "suction" felt through the fitting 91, tube 92, and waste water tubing 55 (see FIG. 4) extending from the brush handle 56. As previously explained, the flexible tubing 54 sheathes, or covers, not only the fresh water supply tubing 53 and the insulated pair of electrical conductors 59 but the waste water tubing 55, as well, although the sheath 54 is not shown in FIG. 4.

Figure 2:
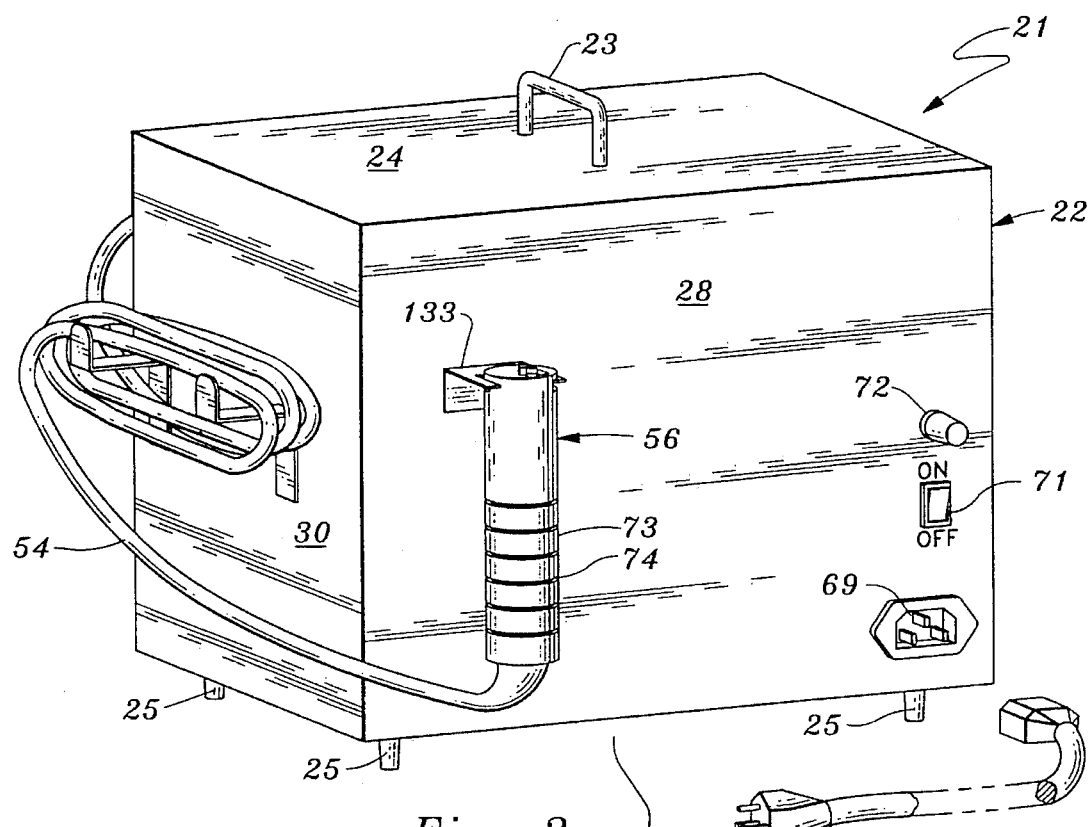
FIG. 2 is a top right rear perspective view of the console disclosing the conduit and the brush handle as well as the power supply and related electrical components.
Figure 8:
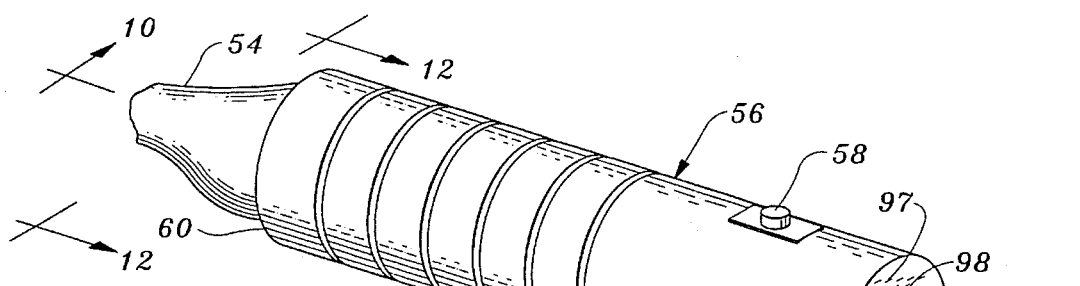
FIG. 8 is a front perspective, to an enlarged scale, of the handle.
Figure 12:
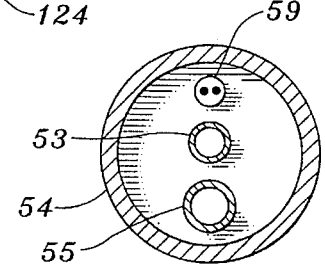
FIG. 12 is a cross-sectional view taken on the line 12—12 in FIG. 8, to an enlarged scale, of the conduit enclosing the fresh water supply tubing, the vacuum line and the electrical conductor leading to the on-off switch in the handle.

At the end of the sheath 54 adjacent the base 60 of the brush handle 56, the sheath 54 is enlarged in size, as best appears in FIGS. 2, 8 and 12, to facilitate connecting the fresh water supply fitting 94 and the waste water return fitting 95, both on the base 60 of the handle 56, to the ends of the respective fresh water tubing 53 and waste water tubing 55. The fitting 100 projecting from the base 60 of the handle 56 carries the insulated pair of conductors 59.

From the base 60, or first end, of the handle 56, a channel 96 formed in the handle 56 extends to a second end 97 in order to carry a supply of fresh water to a fitting 98 projecting forwardly from the second end 97.

In comparable fashion, an internal conduit 101 for the transportation of waste water extends between a fitting 102 on the second end 97 of the handle 56 and the waste water return fitting 95 on the first, or base, end 60 of the handle.

Figure 10:
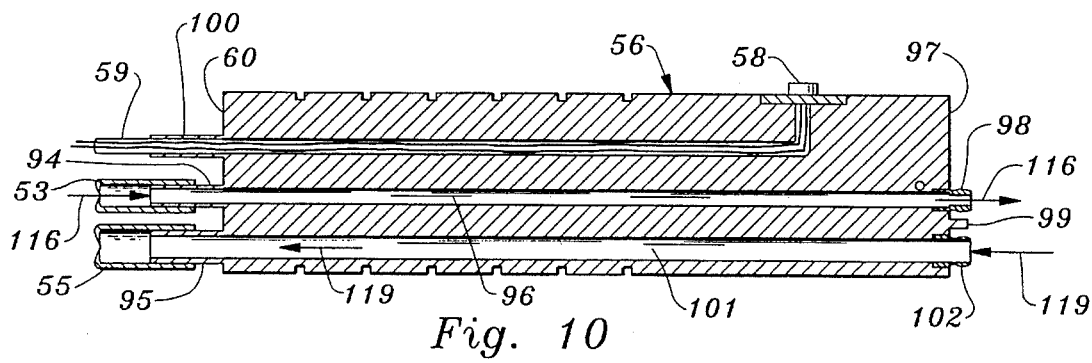
FIG. 10 is a median, vertical, longitudinal section taken on the line 10—10 in FIG. 8, but to a further enlarged scale.

A forwardly projecting plate 99 between the fittings 98 and 102 affords a water barrier (see FIGS. 8 and 10).

The fittings 98 and 102 are in the form of nipples which are provided with elastomeric rings and thus afford a watertight connection to respective fresh water passage 106 and waste water duct 107 in a tooth brush 108.

The tooth brush 108 extends between a butt end 111 and a tip end 112, with the butt end 111 including a blade 113 adapted frictionally to engage the walls of a corresponding recess 114 (see FIG. 8) in the second end 97 of the handle 56 and thus hold the brush firmly in place when the brush 108 is "plugged" into the handle 56. As the brush 108 is "plugged" into the handle, the fresh water fitting 98 on the handle 56 enters the fresh water passage 106 in the brush 108 and thus affords a water-tight flow of fresh water in the direction of the arrows 116 and 117 as shown in respective FIGS. 10 and 11.

Figure 11:
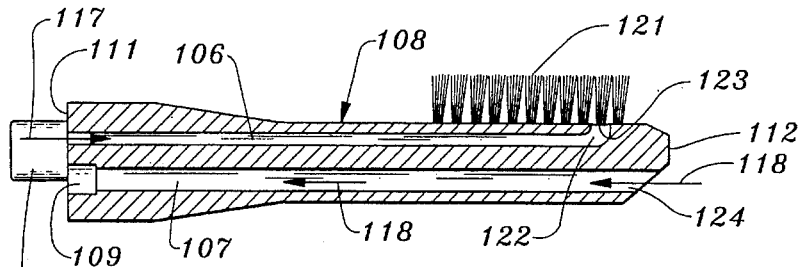
FIG. 11 is a median, vertical, longitudinal section taken on the line 11—11 in FIG. 9 but to a further enlarged scale.

In similar manner, the waste water fitting 102 on the handle 56 enters the portal 109 of the waste water duct 107 on the brush 108 and establishes a water-tight flow of waste water in the direction of the arrows 118 and 119 in respective FIGS. 11 and 10.

Figure 9:
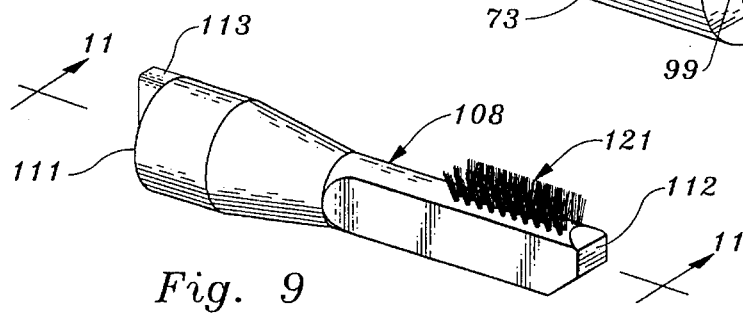
FIG. 9 is a front perspective, to an enlarged scale, of an individual patient's tooth brush.

As best appears in FIGS. 9 and 11, a set of bristles 121 is mounted on the brush 108 adjacent the tip end portion; and the forward, or tip, end 122 of the fresh water passage 106 is directed so that fresh water emerges through a port 123 in the midst of the bristles 121.

Waste water is withdrawn or vacuumed from the tooth and mouth area during the oral hygiene cycle through the tip end opening 124 of the waste water duct 107, in the direction of the arrow 118 in FIG. 11.

Figure 5:
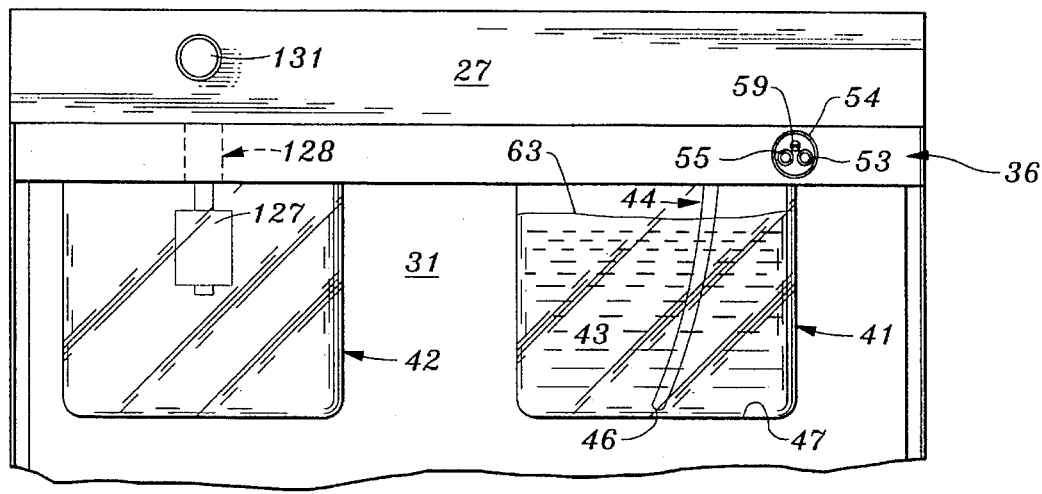
FIG. 5 is a fragmentary front elevation illustrating the position of the fresh water container, on the right, and the waste water container, on the left, at the beginning of the oral hygiene cycle, with the fresh water container substantially full and the waste water container empty.
Figure 6:
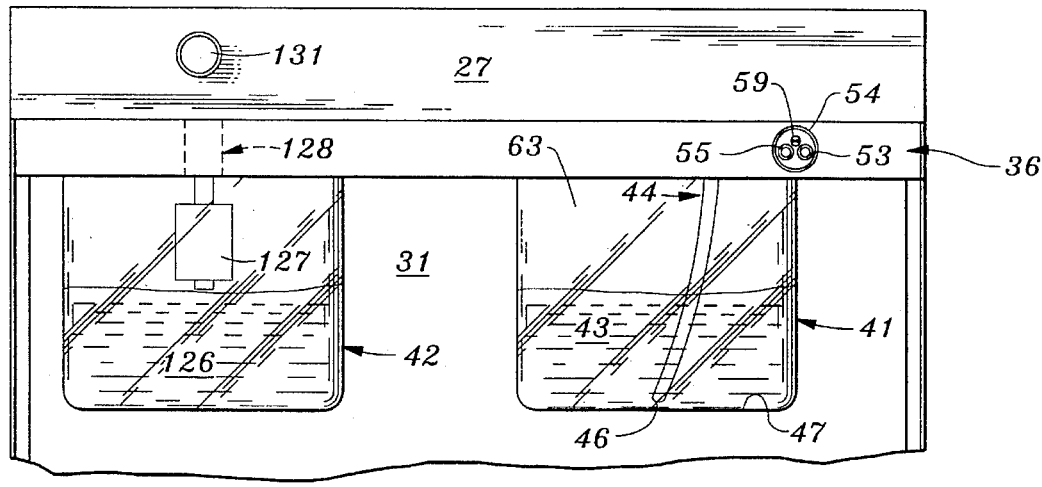
FIG. 6 is a view similar to that of FIG. 5 but showing the water levels in the containers part way through the oral hygiene cycle.
Figure 7:
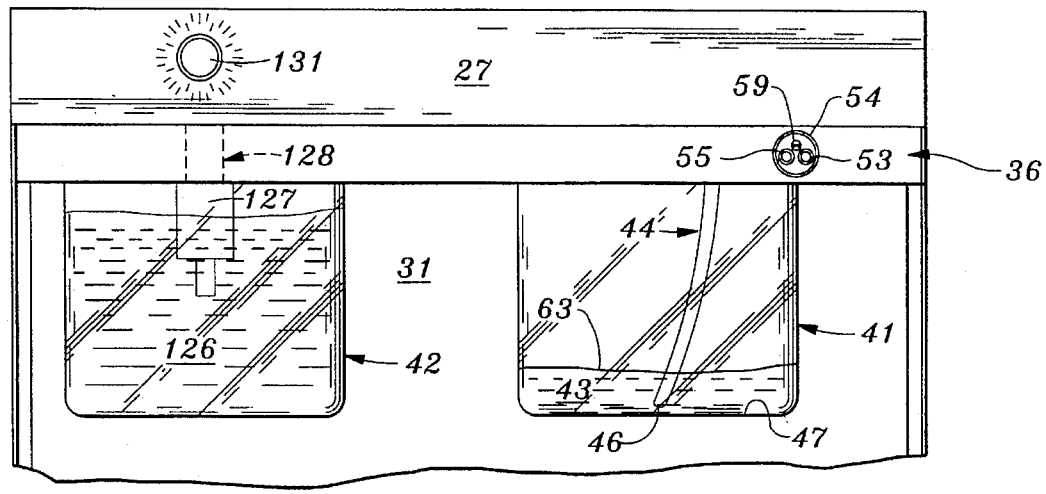
FIG. 7 is a view similar to that of FIGS. 5 and 6 but with the water levels in the containers as they appear at the end of the cycle and with the warning light illuminated to alert the operator that the end of the cycle has been reached.

As the waste water 126 returns through the brush duct 107, the handle conduit 101, tubing 55, tubing 92 and discharges from the fitting 91, the waste water 126 begins to fill the waste water container 42, as appear sequentially in FIGS. 5, 6 and 7.

The rising water level in the waste water bottle 42 elevates a float 127 until it reaches a pre-set "full" position, at which point a float type water level switch 128 (see FIG. 14) is closed, causing an indicator lamp 131 to glow, as simulated in FIG. 7, thereby alerting the operator that the cycle is complete and the waste water bottle 42 needs to be emptied and rinsed or replaced with a new empty bottle. At the same time, the float switch 128 actuates a vacuum pump relay 132 which interrupts the vacuum pump 85 until the waste water bottle 42 is emptied and the float 127 descends by gravity and deactivates the float switch 128 and vacuum pump relay 132.

Concurrently, the water in the fresh water bottle 41 has been depleted, as appears in FIGS. 5, 6 and 7 and must be replenished with fresh water from a sink faucet, or the like.

Figure 13:
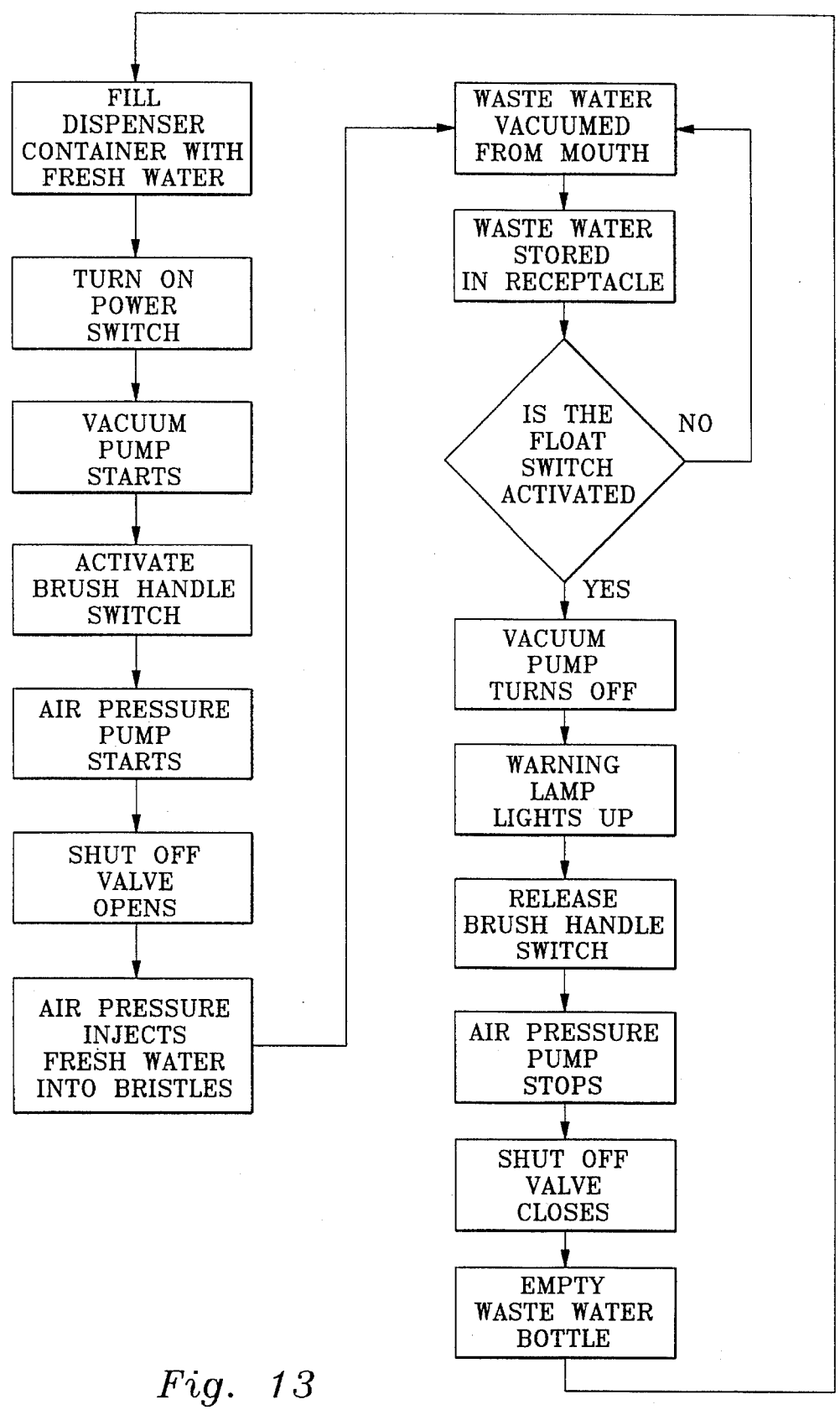
FIG. 13 is a block diagram of the sequence of operations in a typical oral hygiene cycle of the present invention; and, FIG. 14 is a wiring diagram.

With particular reference to the operational cycle illustrated in FIG. 13, it can be seen that as a preliminary step, the dispenser container 41 is filled with fresh water 43 to the approximate level 63 and the waste water receptacle 42 is empty, as illustrated in FIG. 5.

Having placed the console on a level surface adjacent the patient and having plugged the patient's individualized toothbrush 108 onto the handle 56, which has been removed from its support bracket 133 located on the rear panel 28, the toothbrush is positioned so that the tip end 112 of the brush and the bristles 121 can conveniently be placed inside the patient's mouth within a few seconds, or so.

At this juncture, the oral hygiene cycle is commenced by turning on the main power switch 71 on the rear panel 28 of the console 22. This action starts the vacuum pump 85 which begins to remove air from the empty waste water receptacle 42 and discharges the removed air to the atmosphere, in well known fashion.

Then, either with or without the use of a dentifrice on the bristles 121, the tip and bristle portions of the toothbrush 108 are introduced into the patient's mouth. Concurrently, the operator, holding the brush handle 56, activates the brush handle switch 58, thereby starting the fresh water pressure pump 64 which forces pressurized air into the top of the fresh water bottle 41, causing fresh water to flow through the open tip 46 and upwardly in the feed tube 44. Concurrently, the activation of the brush handle switch 58 opens the shut-off valve 57, allowing the fresh water to proceed along the course previously described and to emerge from the port 123 at the base of the forward array of bristles and enter the patient's mouth to provide a plentiful supply of water for the operator's needs in going ahead with the oral hygiene cycle.

While maintaining the handle switch 58 in activating position, the operator deftly cleans the patient's teeth, gums and tongue. Waste water is quickly removed through the opening 124 in the tip portion of the brush 108, as indicated by the arrow 118 in FIG. 11. The waste liquid vacuumed from the mouth is transported to and deposited in the waste water bottle 42.

The cycle ordinarily continues until the vacuum pump 85 has stopped and the warning light 131 glows, indicating that the waste water receptacle 42 has reached its pre-set level for maximum capacity of waste water.

As a practical matter, the size of both of the bottles 41 and 42 is such that adequate water is provided for all but the most unusual requirements of oral hygiene.

When the float switch 128 is actuated, the vacuum pump 85 is automatically turned off and the warning light 131 starts to glow, thereby alerting the operator to release the button switch 58 on the brush handle 56. When the button switch 58 returns to OPEN under spring bias, the air pressure pump 64 is automatically stopped and the shut off valve 57 immediately closes, thereby preventing any further flow of fresh water should there be any residual air pressure in the fresh water bottle 41.

Upon completion of the cycle, the main power switch 71 is turned off and the unit is preferably moved to a convenient location in the vicinity of a sink, or basin, so that the waste water 126 can be rinsed and emptied from the receptacle 42 and fresh water 43 can be introduced into the dispenser bottle 41, and the two bottles returned to their respective threaded sockets in tightly sealed condition in the bottom of the manifold 36.

The operator is then able to move the console to a position close to another patient for initiation of the next oral hygiene cycle as described above.

What is claimed is:

1. Oral hygiene device comprising:

a. a console;

b. a fresh water container mounted on said console to provide a fresh water supply;

c. a waste water container mounted on said console to receive waste water;

d. a tooth brush including an elongated body extending from a butt end to a tip end, said body including a set of bristles adjacent said tip end, a fresh water supply passage extending from said butt end to said tip end and opening in the vicinity of said bristles, and a waste water duct extending from said tip end to said butt end;

e. an elongated handle extending from a first end to a second end, said handle having a fresh water supply channel extending from said first end to said second end and a waste water conduit extending from said second end to said first end;

f. a fresh water tube extending from said fresh water container to said fresh water supply channel at said first end of said handle;

g. a waste water tube extending from said waste water conduit at said first end of said handle to said waste water container;

h. means for detachably mounting said butt end of said tooth brush body on said second end of said handle with said fresh water supply passage in communication with said fresh water supply channel and with said waste water duct in communication with said waste water conduit;

i. means for imposing pressure on the fresh water supply to discharge fresh water in the vicinity of said bristles, said pressure imposing means including an air pressure pump, a power supply connected to said air pressure pump, and a first switch connected to said power supply for selectively activating and deactivating said air pressure pump;

j. means for imposing a vacuum on the waste water to transport waste water in the vicinity of said bristles to said waste water container, said vacuum imposing means including a vacuum pump, a power source connected to said vacuum pump, and a second switch connected to said power source for selectively activating and deactivating said vacuum pump; and, k. manifold means comprising an elongated block mounted on said console and provided with a plurality of inlet fittings and outlet fittings connected to a plurality of internal bores for the predetermined distribution of fresh water and waste water from and toward said fresh water container and said waste water container, respectively.

2. Oral hygiene device as in claim 1 including a transformer and a rectifier connected to said power supply for forming a circuit having low voltage direct current power source, and wherein said first switch is mounted on said handle and is electrically integrated in said low voltage circuit.

3. Oral hygiene device as in claim 2 including a first relay interposed between said power supply and said air pressure pump, said first relay being electrically connected to said first switch and capable of activating and deactivating said air pressure pump.

4. Oral hygiene device as in claim 3 including a fresh water shut off valve interposed in said fresh water tube between said fresh water container and said handle, said first relay being electrically connected to said shut off valve for actuation thereof in response to said first switch on said handle.

5. Oral hygiene device as in claim 1 wherein said second switch is a water level responsive float switch including a float vertically movable in said waste water container, and a second relay interposed between said power supply and said vacuum pump, said float switch being electrically connected to said second relay for selectively actuating and deactuating said vacuum pump in response to the momentary position of said float in said waste water container as determined by the level of the waste water therein.

6. Oral hygiene device as in claim 5 further including a warning lamp electrically connected to said float switch for indicating that the waste water has reached a predetermined elevation.

7. Oral hygiene device as in claims 6 in which said float switch and said warning lamp are electrically integrated in said low voltage circuit.

* * * * *